(12) United States Patent
Mirkin et al.

(10) Patent No.: US 7,466,406 B2
(45) Date of Patent: Dec. 16, 2008

(54) ANALYTE DETECTION USING NANOWIRES PRODUCED BY ON-WIRE LITHOGRAPHY

(75) Inventors: Chad A. Mirkin, Wilmette, IL (US); Lidong Qin, Evanston, IL (US); Can Xue, Evanston, IL (US); Sungho Park, Evanston, IL (US); Ling Huang, Evanston, IL (US)

(73) Assignee: Northwestern University, Evanston, IL (US)

( * ) Notice: Subject to any disclaimer, the term of this patent is extended or adjusted under 35 U.S.C. 154(b) by 393 days.

(21) Appl. No.: 11/372,583

(22) Filed: Mar. 10, 2006

(65) Prior Publication Data

US 2008/0225287 A1   Sep. 18, 2008

Related U.S. Application Data

(60) Provisional application No. 60/741,692, filed on Dec. 2, 2005, provisional application No. 60/661,659, filed on Mar. 14, 2005.

(51) Int. Cl.
*G01J 3/44* (2006.01)
(52) U.S. Cl. ...................... 356/301; 977/762
(58) Field of Classification Search ................ 356/301; 977/762
See application file for complete search history.

(56) References Cited

U.S. PATENT DOCUMENTS 6,970,239 B2   11/2005   Chan et al.

OTHER PUBLICATIONS

Qin, Park, Huang, Mirkin, On-Wire Lithography, www.sciencemag.org, vol. 309, Jul. 2005.*

Cambaz et al., "Anisotropic Etching of SiC Whiskers", Nano Letters, 6(3):548-551 (2005).
Qin et al., "On-Wire Lithography", Science, American Association for the Advancement of Science, US, 309(113):113-115 (2005).
Sioss et al., "Batch Preparation of Linear Au and Ag Nanoparticle Chains via Wet Chemistry", Nano Letters, 5(9):1779-1783 (2005).
International Search Report dated Mar. 13, 2007 for International Application No. PCT/US2006/037503.
Written Opinion of the International Searching Authority for International Application No. PCT/2006/037503.
Adrian, *J. Chem. Phys.*, 77(11):5302-5314 (1982).
Cao et al., *Science*, 297:1536-1540 (2002).
Cao et al., *J. Am. Chem. Soc.*, 125:14676-14677 (2003).
Doering et al., *Anal. Chem.*, 75:6171-6176 (2003).
Draine et al., *User Guide for the Discrete Dipole Approximation Code DDSCAT.6.0*, pp. 1-46 (2003) as found at http://arxiv.org/abs/astro-ph/0309069.
Freeman et al., *Science*, New Series, 267(5204):1629-1632 (1995).
Fromm et al., *Nano Letters*, 4(5):957-961 (2004).
Futamata et al., *J. Phys. Chem.*, 107:7607-7617 (2003).
Gate et al., *Chem. Rev.*, 105:1171-1196 (2005).

(Continued)

*Primary Examiner*—L. G Lauchman
(74) *Attorney, Agent, or Firm*—Marshall, Gerstein & Borun LLP

(57) ABSTRACT

The present invention relates to methods of detecting analytes using nanowires having nanodisk arrays. In particular, the present invention discloses methods of detecting analytes via surface enhanced Raman scattering (SERS) and employing nanowires prepared using on-wire lithography (OWL).

15 Claims, 6 Drawing Sheets

OTHER PUBLICATIONS

Ginger et al., *Angew. Chem. Int. Ed.*, 43:30-45 (2004).
Gunnarsson et al., *Applied Physics Letters*, 78(6)802-804 (2001).
Haynes et al., *Anal. Chem.*, 77:338A-346A (2005).
Hao et al., *J. Chem. Phys.*, 120:357-366 (2004).
Jeanmaire et al., *J. Electroanal. Chem.*, 84:1-20 (1977).
Jiang et al., *J. Phys. Chem.*, 107:9964-9972 (2003).
Kelly et al., *J. Phys. Chem.*, 107:668-677 (2003).
Kneipp et al., *Phys. Rev. Lett.*, 78:1667-1670 (1997).
Kneipp et al., *Analytical Chemistry*, 77(8):2381-2385 (2005).
Kovtyukhova et al., *Chem. Eur. J.*, 8:4354-4363 (2002).
Lee et al., *J. Am. Chem. Soc.*, 128:2200-2201 (2006).
Li et al., *Applied Physics Letters.*, 77(24):3995-3997 (2000).
Lu et al., *Nano Letters*, 5(1):119-124 (2005).
Maier et al., *Nature*, 2:229-232 (2003).
Martin, *Science*, 266:1961-1966 (1994).
Michaels et al., *J. Phys. Chem.*, 104:11965-11971 (2000).
Nicewarner-Pena et al., *Science*, 294:137-141 (2001).
Nie et al., *Science*, 275:1102-1106 (1997).
Orendorff et al., *Anal. Chem.*, 77:3261-3266 (2005).
Oubre et al., *J. Phys. Chem.*, 109:10042-10051 (2005).
Park et al., *Applied Physics Letters*, 75(2):301-303 (1999).
Park et al., *Science*, 303:348-351 (2004).
Park et al., *J. Am. Chem. Soc.*, 126:11772-11773 (2004).
Piner et al., *Science*, 283:661-663 (1999).
Qin et al., *Science*, 309:113-115 (2005).
Reed et al., *Science*, 278:252-254 (1997).
Reichert et al., *Physical Review Letters*, 88(17):176804-1 through 176804-4 (2002).
Routkevitch et al., *J. Phys. Chem.*, 100:14037-14047 (1996).
Salem et al., *Nano Letters*, 4(6):1163-1165 (2004).
Stuart et al., *Analytical Chemistry*, 77(13):4013-4019 (2005).
Talley et al., "*Nano Letters*, 5(8):1569-1574 (2005).
Wang et al., *J. Am. Chem. Soc.*, 127:14992-14993 (2005).
Xiang et al., *Angew. Chem. Int. Ed.*, 44:1265-1268 (2005).
Xu et al., *Physical Review Letters*, 83(21):4357-4360 (1999).
Zou et al., *Chemical Physics Letters*, 403:62-67 (2005).

\* cited by examiner

ANALYTE DETECTION USING NANOWIRES PRODUCED BY ON-WIRE LITHOGRAPHY

CROSS-REFERENCE TO RELATED APPLICATIONS

This application claims the benefit of U.S. Provisional Application Ser. No. 60/661,659, filed Mar. 14, 2005, and U.S. Provisional Application Ser. No. 60/741,692, filed Dec. 2, 2005.

STATEMENT OF GOVERNMENTAL INTERESTS

This invention was made with government support under Defense Advanced Research Projects Agency (DARPA) and Air Force Office of Scientific Research (AFOSR) grant No. FA9550-05-1-0348, and National Science Foundation grants No. EEC-0118025 and No. DMR-0076097. The government has certain rights in this invention.

FIELD OF THE INVENTION

The present invention relates to methods of using nanowires and Raman spectroscopy to detect an analyte. In particular, the present invention relates to on-wire lithographic methods of forming nanodisk arrays and methods of using these nanodisk arrays in Raman spectroscopy detection of an analyte.

BACKGROUND OF THE INVENTION

Surface Enhanced Raman Scattering (SERS) was first demonstrated in 1977 (Jeanmaire et al., *J Electroanal Chem* 84: 1 (1977)). SERS significantly increased the magnitude of a Raman scattering signal by functionalizing a molecule onto a rough metal surface (Haynes et al., *Anal Chem* 77: 338A (2005)). It also has been reported that using metal nanoparticles as substrates in SERS provided for $10^{14}$ increased signal (Kniepp et al., *Phys Rev Lett* 78: 1667 (1997) and Nie et al., *Science* 275: 1102 (1997)). This advancement made single molecule detection possible and showed promise in biological detection applications (Cao et al., *Science* 297: 1536 (2002); Cao et al., *J Am Chem Soc* 125: 14676 (2003); and Doering et al., *Anal Chem* 75: 6171 (2003)). In the investigation of single molecule and single particle SERS, researchers have found that some particles demonstrated a much higher enhancement, which were labeled "hot spots." Although researchers in the field reported the identification of various Raman hot spots, no work has reported a systematic study of Raman hot spots.

Substrates previously used for SERS applications include roughened metal surfaces, such as those reported in U.S. Pat. No. 6,970,239. No control over the roughened surface or of the porous characteristics of the metal surface was disclosed. Because the porosity of the metal surface is theorized to be a major factor in the enhancement of Raman scattering, control over the characteristics of the metal surface is needed both to better understand the role porosity plays in the enhancement and to provide optimum surface characteristics for SERS detection of analytes. Optimization may provide an ability to detect small, even single molecule, amounts of an analyte of interest.

SUMMARY

The present invention relates to methods of detecting analytes employing nanowires having nanodisk arrays. Therefore, one aspect of the present invention is to provide methods for detecting the presence and/or concentration of an analyte of interest in a sanple using nanowires having nanodisk arrays and various spectroscopy techniques. The nanowires are synthesized using on-wire lithography (OWL) such that the nanodisk thicknesses and the gaps between the nanodisks are precisely controlled to achieve a highly ordered and tailorable nanowire. Depending upon the analyte of interest, the nanowire can be specifically tuned for detection of that analyte. The analyte of interest can be detected either directly or indirectly via a detection reagent or probe. In some embodiments, the spectroscopic method employed is Raman spectroscopy and the nanowire enables surface-enhanced Raman scattering (SERS). In other embodiments, the spectroscopic method is fluorescence. Microwave detection can also be used.

Another aspect of the present invention is to provide a kit comprising nanowires having different nanodisk arrays such that different analytes of interest can be detected by selection of a proper nanowire. In some embodiments, the kit comprises nanowires having repeating units of nanodisk arrays having the same characteristics (e.g., disk thickness, gap spacing between disks, and separation spacing between nanodisk arrays), in addition to a plurality of nanowires having different characteristics from one another. In other embodiments, the kit comprises nanowires having different nanodisk arrays along the same nanowire. The kit also can comprise nanowires having repeating nanodisk arrays and nanowires of varying nanodisk arrays.

DETAILED DESCRIPTION OF THE PREFERRED EMBODIMENTS

Figure 1:
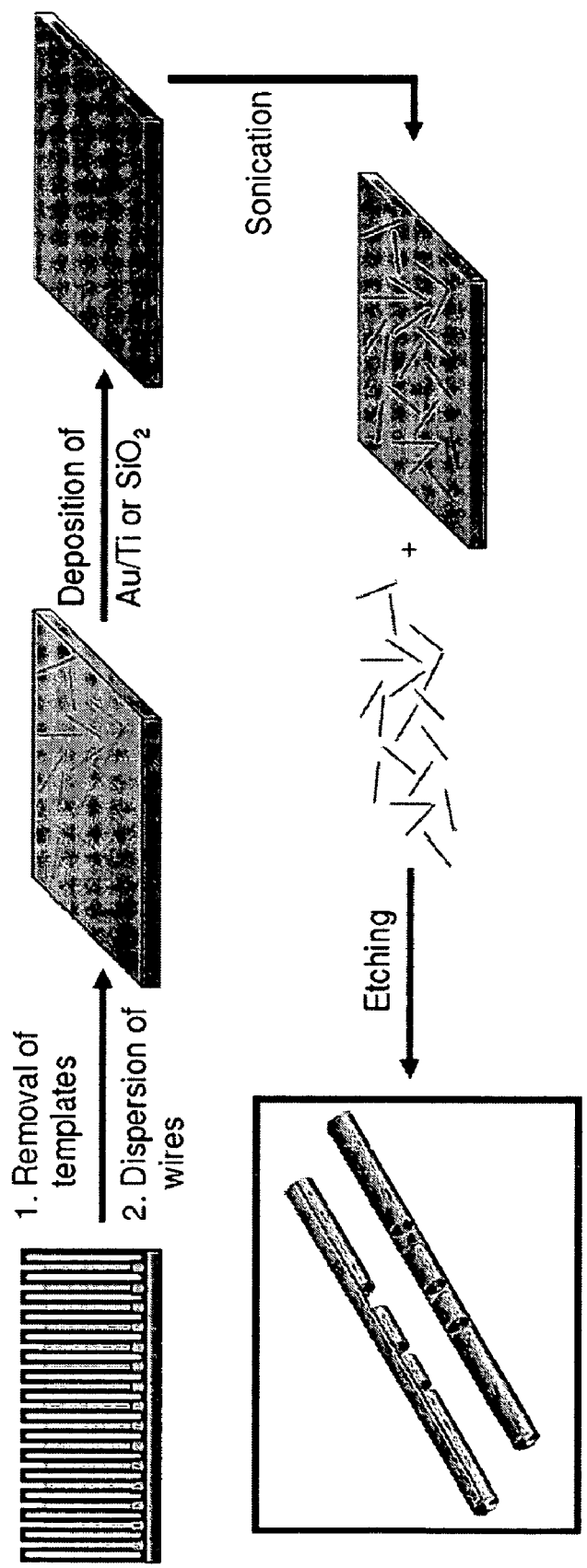
FIG. 1 is a schematic of the on-wire lithography (OWL) process.

The present invention is directed to methods of detecting analytes using spectroscopy methods, such as Raman, fluorescence, UV, and the like. The following disclosure is primarily directed to Raman but can be readily extended to other spectroscopic methods. More particularly, the present invention provides methods of detecting analytes via Raman spectroscopy using nanodisk arrays having various electronic, chemical, and physical characteristics. Nanodisk arrays having the appropriate characteristics allow for the enhancement of Raman signals. The enhanced Raman signal can be correlated to the presence or concentration of an analyte in a test sample.

When certain molecules are illuminated, a small percentage of the molecules which have retained a photon do not return to their original vibrational level after remitting the retained photon, but drop to a different vibrational level of the ground electronic state. The radiation emitted from these molecules is at a different energy and hence a different wavelength. This is referred to as Raman scattering.

If the molecule drops to a higher vibrational level of the ground electronic state, the photon emitted is at a lower energy or longer wavelength than that retained. This is referred to as Stokes-shifted Raman scattering. If a molecule is already at a higher vibrational state before it retains a photon, it can impart this extra energy to the remitted photon thereby returning to the ground state. In this case, the radiation emitted is of higher energy (and shorter wavelength) and is called anti-Stokes-shifted Raman scattering. In any set of molecules under normal conditions, the number of molecules at ground state is always much greater than those at an excited state, so the odds of an incident photon hitting an excited molecule and being scattered with more energy than it carried upon collision is very small. Therefore, photon scattering at frequencies higher than that of the incident photons (anti-Stokes frequencies) is minor relative to that at frequencies lower than that of the incident photons (Stokes frequencies). Consequently, it is the Stokes frequencies that are usually analyzed.

The amount of energy lost to or gained from a molecule in this way is quantized, resulting in scattered photons having discrete wavelength shifts. These wavelength shifts can be measured by a spectrometer. Raman spectroscopy is one useful analytical tool to identify certain molecules, and as a means of studying molecular structure. Other useful spectroscopic methods include fluorescence, infrared, nuclear magnetic resonance, and the like.

A significant increase in the intensity of Raman light scattering can be observed when molecules are brought into close proximity to (but not necessarily in contact with) certain metal surfaces. The increase in intensity can be on the order of several million-fold or more, and has been coined "surface enhanced Raman scattering" (SERS).

The cause of the SERS effect is not completely understood. However, at least two separate factors have been identified as contributing to SERS. First, metal surfaces often contain minute irregularities, which can be thought of as spheres. Those irregularities having diameters of approximately $\frac{1}{10}$th the wavelength of the incident light are considered to contribute most to the effect. The incident photons induce a field across the particles which have very mobile electrons (due to the nature of metals).

In certain configurations of metal surfaces or particles, groups of surface electrons can be made to oscillate in a collective fashion in response to an applied oscillating electromagnetic field. Such a group of collectively oscillating electrons is called a "plasmon." The incident photons supply this oscillating electromagnetic field. The induction of an oscillating dipole moment in a molecule by incident light is the source of the Raman scattering. The effect of the resonant oscillation of the surface plasmons is to cause a large increase in the electromagnetic field strength in the vicinity of the metal surface. This results in an enhancement of the oscillating dipole induced in the scattering molecule and hence increases the intensity of the Raman scattered light. The effect is to increase the apparent intensity of the incident light in the vicinity of the particles.

A second factor contributing to the SERS effect is molecular imaging. A molecule having a dipole moment and in close proximity to a metallic surface will induce an image of itself on that surface of opposite polarity (i.e., a "shadow" dipole on the plasmon). The proximity of that image is thought to enhance the ability of the molecules to scatter light. The coupling of a molecule having an induced or distorted dipole moment due to the surface plasmons greatly enhances the excitation probability and results in an increase in the efficiency of Raman light scattered by the surface-absorbed molecules.

The SERS effect can be enhanced through combination with the resonance Raman effect. The surface-enhanced Raman scattering effect is even more intense if the frequency of the excitation light is in resonance with a major absorption band of the molecule being illuminated. The resultant Surface Enhanced Resonance Raman Scattering (SERRS) effect can result in an enhancement in the intensity of the Raman scattering signal of seven orders of magnitude or more.

On-wire lithography (OWL) is a nanofabrication strategy which is capable of achieving 2.5 nm, and in some instances 1 nm, resolution and 20 nm feature size on a nanowire. OWL provides a method for producing nanodisk arrays which can be used for SERS applications. The nanodisk array substrate can have several features that make it a unique SERS substrate, including easy functionalization on a single nanowire, easy homogeneous suspension in dye solutions for SERS studies, and large surface area and chemical potential for functionalization. The high resolution and flexibility of the nanodisk array allows for systematic study of plasmon resonance of the particles. The use of substrates obtained via OWL reduces the potential effect of imperfections on the metal surface, thereby allowing for a focused study on the molecular imaging effect. No other lithography technique has provided substrates for a SERS study that allows for this type of systematic study.

As used herein, "nanorods" refers to small structures that are less than 10 µm, and preferably less than 5 µm, in any one dimension and that have a length to width ratio greater than one. The nanorods used in the present invention are multicomponent in nature. As used herein, "multicomponent" refers to an entity that comprises more than one type of material. For example, a multicomponent nanorod refers to a nanorod having sections of different materials, e.g., a nanorod with one or more Au segments and one or more Ni segments.

The metal component of the nanorod can be any metal compatible with in situ electrochemical deposition. Examples of such metals include, but are not limited to, indium-tin-oxide, titanium, platinum, titanium tungstide, gold, silver, nickel, copper, and mixtures thereof.

Figure 2:
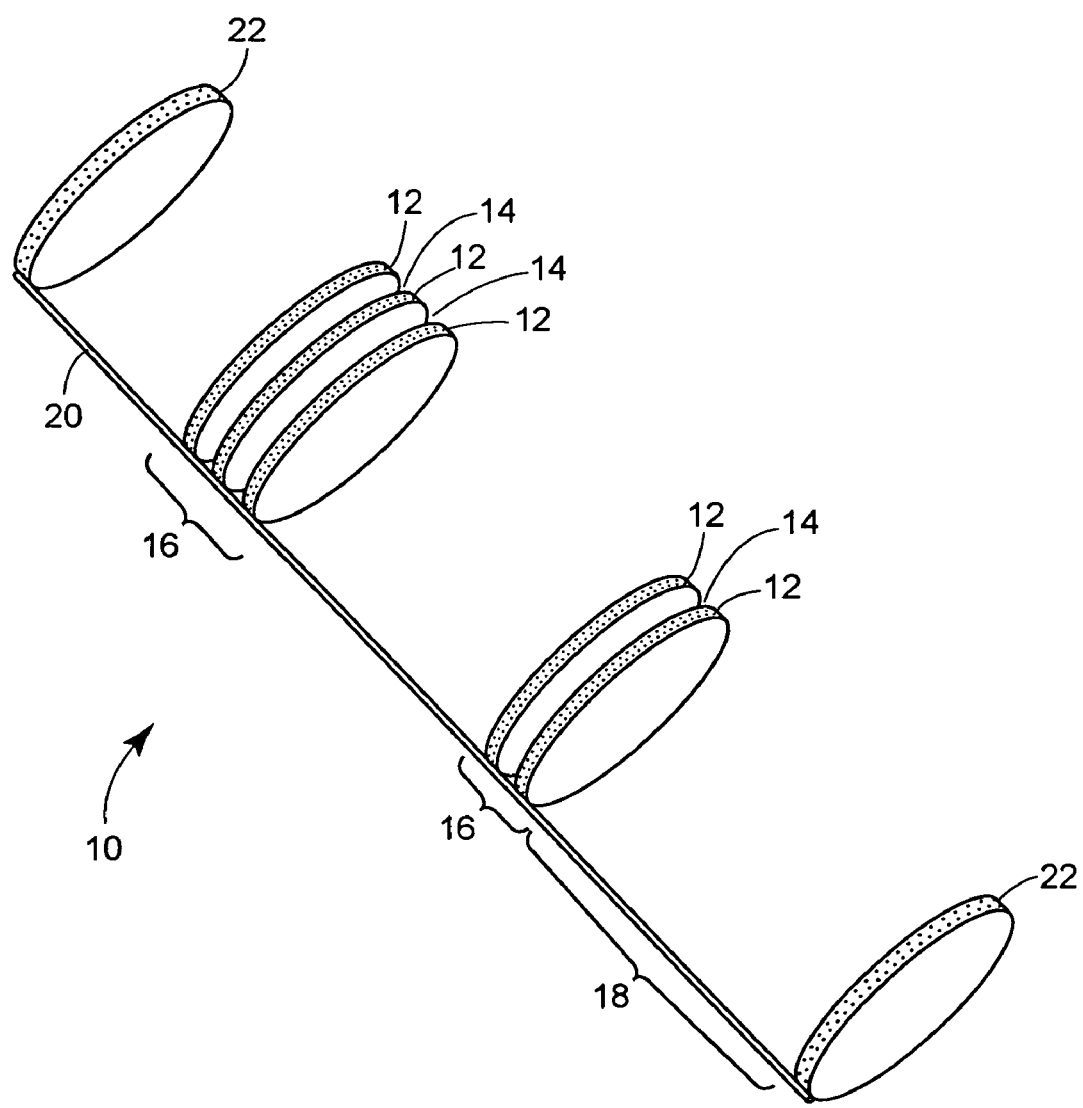
FIG. 2 is a schematic of a nanowire 10, showing a nanodisk 12, a gap 14 between nanodisks to form a nanodisk array 16, a separation gap 18 between nanodisk arrays, a coating 20 to hold the nanodisks together, and two capping nanodisks 22 at each end of the nanowire 10.

A "nanowire," interchangeably referred to as a "gapped nanowire," is a nanorod that has been subjected to etching to remove certain metal segments and leave behind others. FIG. 2 shows a nanowire 10 with its various components. These nanowires have electronic properties that can be tailored from their compositional components (i.e., the identities of the metals forming the nanorod). The use of metals having different chemical and electrical properties allows the creation of gaps in these nanowires when the nanowire is treated with a solution that dissolves one metal of the nanorod while the other metal is unaffected. In FIG. 2, these nanogaps 14 are useful in producing nanodisk arrays 16 of various thicknesses that can be used to assess electromagnetic response for SERS experiments.

A nanodisk array is a series of metal segments (i.e., nanodisks) separated by a gap. A nanodisk array 16 is shown in FIG. 2. In some cases, the gap is between about 2 nm and about 500 nm. Other gap ranges contemplated include in the range of about 5 and about 160 nm. Specific examples of gap sizes include 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, and 500 nm. In other cases, the gap is greater than 500 nm. Gaps up to an including 2 µm may also be incorporated into a nanodisk array.

The metal segments remaining after etching form nanodisks 12, as illustrated in FIG. 2. Disk thicknesses for nanodisks include, but are not limited to, ranges of about 20 nm to about 500 nm, about 40 nm to about 250 nm, and about 50 nm to about 120 nm. Specific disk thickness contemplated for use in the present invention include 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 310, 320, 330, 340, 350, 360, 370, 380, 390, 400, 410, 420, 430, 440, 450, 460, 470, 480, 490, and 500 nm. In some cases, the disk thickness of the nanodisk is at least 500 nm and can be up to 2 µm.

A series of nanodisk arrays having different characteristics (e.g., disk thickness and gap size) may be present on the same nanowire. Separation of the nanodisk arrays on a nanowire is achieved using separation gaps 18, as illustrated in FIG. 2. The length of a separation gap is dependent upon the size of the nanodisk array. Typically, a separation gap is at least two times greater, preferably three times greater, than the total length of a nanodisk array. For example, a nanodisk array composed of two 120 nm disks separated by a 50 nm gap can be separated from a second nanodisk array by a separation gap of about 1 µm. For nanodisk arrays having larger disk thickness and gaps, larger separation gaps are needed. Nanodisk arrays of varying characteristics on the same nanowire are illustrated, for example, in FIG. 4D.

The number of gaps in a nanodisk array can vary. At least one gap must be present in a nanodisk array. Gaps numbering from 1, 2, 3, 4, 5, 6, 7, 8, 9, and 10 can all be incorporated into a nanodisk array. The number of gaps in a nanodisk array determines the number of nanodisks in the array. For example, one gap correlates to two nanodisks; two gaps correlate to three nanodisk; and three gaps to four nanodisks.

As used herein, the term "sacrificial metal" refers to a metal that can be dissolved under the proper chemical conditions. Examples of sacrificial metals include, but are not limited to, nickel which is dissolved by nitric acid, and silver which is dissolved by a methanol/ammonia/hydrogen peroxide mixture.

As used herein, the term "etching" refers to a process of dissolving a sacrificial metal segment using conditions suitable for dissolving or removing the metal comprising the sacrificial segment. As mentioned above, such etching solutions include, but are not limited to, nitric acid and a methanol/ammonia/hydrogen peroxide mixture.

As used herein, "coating" refers to a material that is positioned to contact one side of a multicomponent nanorod, prior to the etching step. The purpose of the coating is to provide a bridging substrate to hold segments of the etched nanorod (i.e., a nanowire) together after removal of the intervening sacrificial metal segments in the etching process. Nonlimiting examples of coatings used in this invention include a gold/titanium alloy and silica. A coating with a gold/titanium alloy allows for the nanowire to conduct an electrical current, whereas a silica coating electrically isolates the various nanodisk arrays from each other. Other backings may be chosen to provide other electrical, chemical, or physical characteristics to the nanowire, depending upon the end use of the nanowire.

The effect of electromagnetic field on SERS can be studied using the OWL generated nanodisk arrays. OWL is based upon manufacturing segmented nanowires comprising at least two materials, one that is susceptible to, and one that is resistant to, wet chemical etching. There are a variety of material pairs that can be used. Au—Ag and Au—Ni are two such examples of metal pairs of differing chemical properties. The sacrificial metal in these pairs are Ag and Ni, respectively. However, any combination of metals having contrasting susceptibility to chemical etching conditions may be used.

The surfaces of nanodisks are clean, i.e., free from contamination of stabilizing surfactants or other organic chemicals, because the OWL synthetic process uses nitric acid which removes essentially all organic compounds from the surface of the nanodisks. This clean surface allows for better functionalization and also decreases Raman scattering noise attributed to surface contaminants. Detection of small analyte concentrations or probe molecules therefore is enhanced due to the decreased scattering noise and tailorable functionalization of the nanodisks.

Different metals can be incorporated into the nanodisks by simple modifications to the synthesis. Nonlimiting examples of metals that can be incorporated include silver (Ag), gold (Au), and copper (Cu), which are particularly useful as SERS substrates. SERS substrates are interchangeably referred to as SERS active substrates herein.

The presence of photoexcitable surface plasmons in a substrate is generally considered necessary for surface enhancement. In order for surface plasmons to surface so that plasmon emission can exhibit a SERS effect, surface plasmons must be localized so that their resident energy is not dispersed. Suitable SERS substrates include, but are not limited to, the nanogap wires/nanodisk arrays produced via OWL.

In an analysis of a sample containing or suspected of containing an analyte of interest, the sample is attached onto a SERS-active substrate (i.e., a nanowire). An analyte can be attached to the SERS-active surface by direct adsorption, adsorption through a linker arm covalently attached to the analyte, or by the covalent attachment of the analyte to a detection reagent or probe on the SERS-active surface directly, through a linker arm, or by intercalation of the distal portion of a linker arm into the enhancing surface. A radiation source is selected to generate radiation having a wavelength that causes appreciable Raman scattering in the presence of the analyte being measured. Although it is known that Raman scattering occurs at all wavelengths, the radiation typically employed will be near infrared radiation because ultraviolet radiation often causes fluorescence.

Detection of an analyte can proceed either directly or in combination with a detection reagent or probe. In certain cases, the analyte does not have an appreciable Raman scattering cross section and a detection reagent or probe is needed to provide sufficient Raman scattering for detection. The detection reagent or probe can be a molecule having one or more, preferably ally, of the following properties: (a) a strong absorption band in the vicinity of an excitation wavelength (extinction coefficient near $10^4$ or greater); (b) a functional group which will enable it to be covalently or non-covalently bound to an analyte of interest; (c) photostability; (d) sufficient surface and resonance enhancement to allow detection limits of at least 10 μg, and preferably in the subnanogram range; (e) minimal exhibition of strong fluorescence emission at the excitation wave length used, usually denoted as having a large Stokes shift; and (f) a relatively simple scattering pattern with a few intense peaks. When more than one label is used, it is preferred that the labels having spectral patterns which do not interfere with one another, e.g., overlap, so several indicator molecules can be analyzed simultaneously. In some embodiments, spectral overlap is a desired characteristic because the emission spectrum from one detection reagent or probe can overlap the excitation spectrum of another, exciting the first detection reagent or probe and resulting in a "pumping" of the second.

Examples of detection reagents or probes include, but are not limited to, 4-(4-aminophenylazo)phenylarsonic acid monosodium salt, arsenazo I, basic fuchsin, Chicago sky blue, direct red 81, disperse orange 3,2-(4-hydroxyphenylazo)-benzoic acid (HABA), erythrosin B, trypan blue, ponceau S, ponceau SS, 1,5-difluoro-2,4-dinitrobenzene, methylene blue (MB), and p-dimethylaminoazobenzene (PMA). In some embodiments, the detection reagent or probe can be covalently attached to the analyte of interest. In other embodiments, the detection reagent or probe can be non-covalently attached to the analyte of interest, e.g., via hybridization, pi-stacking, hydrogen bonding, van der Waals interactions, chelation, and the like.

The radiation source can be any source that provides the necessary wavelength to excite the analyte or detection reagent or probe for detection using Raman spectroscopy. Typically, a laser serves as the excitation source. The laser may be of an inexpensive type, such as a helium-neon or diode laser. In some embodiments, a narrow bandwidth, high frequency, amplitude and modal stability, and no sidebands or harmonics are important characteristics of the laser. Lamps also can be used. The radiation sources used can be monochromatic or polychromatic, and also can be of high intensity. In one embodiment, the radiation source provides a high enough photon flux that the Raman transitions of the analyte or detection reagent or probe are saturated, in order to maximize the SERS signal.

Several methods are available for detecting Raman scattering. These methods generally can be used with different types of spectrometers. In SERS, the primary measurement is one of light scattering intensity at particular wavelengths. SERS requires measuring wavelength-shifted scattering intensity in the presence of an intense background from the excitation beam. The use of a Raman-active substance having a large Stokes shift simplifies this measurement. Methods for further simplifying the readout instrument are contemplated, such as the use of wavelength selective mirrors or holographic optical elements for scattered light collection.

Neither the angle of the incident light beam to the surface nor the position of the detector is critical for SERS analysis. With flat surfaces, positioning the surface of the excitation source at 60 degrees to the normal is typical, and detection at either 90 degrees or 180 degrees to the source is standard. SERS excitation can be performed in the near infrared range, which minimizes excitation of intrinsic sample fluorescence. SERS-based ligand binding assays using evanescent waves propagated by optical waveguides can also be performed. For non-flat surfaces, the wavelength and angle are important and give rise to scattering.

No signal development time is required as readout begins immediately upon illumination and data can be collected for as long as desired without decay of signal unless the excitation light is extremely intense and chemical changes occur. Unlike fluorescent readout systems, SERS reporter groups will not self-quench so the signal can be enhanced by increasing the number of Raman active reagent molecules. Fluorescent molecules near the SERS-active surface will actually be surface-quenched. The SERS effect can be excited by direct illumination of the surface or by evanescent waves from a waveguide beneath the plasmon-active surface.

The nanodisk array characteristics also can be tuned to provide means for detecting analytes using other spectroscopic means. Smaller disk thicknesses (e.g., less than 400 nm) and gaps (e.g., less than 100 nm) are more suitable for optics detection (Raman spectroscopy, fluorescence, and the like), while larger disk thicknesses (e.g., between about 500 nm and about 2 μm) and gaps (e.g., between about 100 nm and about 1 μm) are more suitable for microwave applications. Depending upon the excitation and detection method, the nanodisk array of the nanowire can be tailored to provide optimum characteristics. In one embodiment, the spacing of the nanodisk arrays are set at odd multiples of one-fourth the wavelength in order to produce a resonant cavity that enhances the field strength; even multiples do not enhance, but rather, suppress emissions.

In another embodiment, the nanowires are selected to enhance a fluorescence signal of an analyte or a detection reagent or probe. In some cases, the fluorescence of the detectable molecule (either the analyte of interest or a detection reagent or probe) is measured. In this case, the fluorescence signal indicates the presence or absence of an analyte. The excitation and emission wavelengths are selected based upon the characteristics of the fluorescent moiety to be detected. In the case where a detection reagent or probe is needed (e.g., the analyte of interest is not fluorescent), then the wavelengths are selected such that the detection reagent or probe can fluoresce. The nanodisk array characteristics (e.g., disk thickness and gap size) are selected to enhance the fluorescent signal of the analyte or detection reagent or probe. The selection of the nanowire having the proper nanodisk array is readily performed by persons skilled in the art using simple trial techniques. For example, in one embodiment, the characteristics are calculated based upon the wavelengths of radiation and the effective refractive index of the medium between the nanodisks.

In order to determine the concentration of an analyte in a test sample, it is necessary to correlate a measured signal to the analyte concentration. Quantification can be accomplished either by inclusion of known concentrations of one or more molecules (for example, an internal standard) or by referencing the signal intensity of an unknown amount of an analyte of interest with a standard curve generated from measurement of known amounts of that analyte. Techniques well known to those of skill in the art can be used in the creation of a standard curve and in the calculations of the concentration of the analyte of interest.

In accordance with an important feature of the present invention, a kit comprising two or more items useful for practicing a method of the invention is provided. For example, in one variation, the kit comprises containers having (a) detection reagents or probes or (b) a plurality of nanowires, wherein each nanowire comprises at least one nanodisk array. In some embodiments, the nanowire comprises repeating units of the same nanodisk array. In other embodiments, the nanowire comprises nanodisk arrays of different properties, e.g., different disk thicknesses, different gap sizes, and/or different coatings. Regardless of the type of nanowire, the nanodisk arrays are separated from each other by distances sufficient to isolate each disk array from an adjacent nanodisk array. In some cases, the kit further comprises a container having detection reagents or probes, such as 4-(4-aminophenylazo)phenylarsonic acid monosodium salt, arsenazo I, basic fuchsin, Chicago sky blue, direct red 81, disperse orange 3, HABA, erythrosin B, trypan blue, ponceau S, ponceau SS, 1,5-difluoro-2,4-dinitrobenzene, MB, and PMA. In certain cases, it is not necessary to know the optimal properties for detection of the analyte of interest, because a plurality of nanodisk arrays are provided along the same nanowire or in a mixture of nanowires of different properties. Exposure to the appropriate excitation wavelength results in SERS on a nanowire having a nanodisk array with characteristics compatible with those of the analyte of interest.

In another aspect of the present invention, the nanowires can be used for any application wherein field intensification caused by a plasmon resonance and/or a controlled, tuned cavity is useful. Such applications include photonic crystal technologies, fluorescence measurements, and coupler/translator applications. In some cases, the nanowires are constructed such that the spacing between nanodisks is suitable for microwave wavelengths. In other cases, the spacing is suitable for infrared wavelengths, and in still other cases, the spacing is suitable for visible or ultraviolet wavelengths.

The disclosed nanowires can be used in photonic crystals. Photonic crystals are processed materials with periodic spatial variations of the dielectric constant. Based on a Bragg reflection, electromagnetic waves having defined frequency ranges cannot pass through the photonic crystal and, therefore, no resonant modes can occur. These frequency intervals are referred to as photonic band gaps. The energy does not spread in predefined directions within this stop band. In other words, photonic crystals are artificial crystal structures that have an effect on electromagnetic waves that is similar to the effect a semiconductor crystal has on electronic waves. Light propagation in a photonic crystal can be controlled based on the material and the photonic crystal structure. As the nanowires of the present invention have periodic structures, they can be used as photonic crystals.

Additional aspects and details of the invention will be apparent from the following examples, which are intended to be illustrative rather than limiting.

EXAMPLES

On-Wire Lithography Process

The metal segments are electrochemically deposited in porous alumina templates in a controlled fashion from suitable plating solutions via well-established methods (Martin, *Science,* 266, 1961, 1994; Routkevitch et al, *J. Phys. Chem.,* 100, 14037, 1996; Nicewamer-Pena et al, *Science,* 294, 137, 2001; Kowtyukhova et al, *Chem. Eur. J.,* 8, 4354, 2002). The length of each segment is tailored by controlling the charge passed during the electrodeposition process. The resulting multi-metallic wires then are released from the template by dissolution of the template via known procedures (Park et al, *Science,* 303: 348, 2004).

In one example, an aqueous suspension of Au—Ni nanorods is cast upon a glass microscope slide pre-treated with a piranha solution which makes the slide more hydrophilic. After drying, a layer of silicon dioxide is deposited on the nanorods, using plasma enhanced chemical vapor deposition (PECVD). This resulted in one side of the nanorod being coated with silicon dioxide while the other side, which is protected by the microscope slide substrate, remained uncoated. Sonication of the substrate leads to the release of the coated nanorods into solution. The final step of the OWL process involves the selective wet-chemical etching of the sacrificial segments.

Nickel segments can be removed from the rods by treating the rods with concentrated nitric acid for one hour (hr). This results in the generation of nanowire structures with gaps precisely controlled by the length of the original Ni segments. The Au segments remaining after removal of the Ni segments are held in place by the stripe of silicon dioxide. Because silicon dioxide is an insulator, the Au segments are electrically isolated from one another. Alternatively, the Au segments can be electrically connected to one another by coating the nanowires with Au/Ti rather than silicon dioxide in this process.

In another alternative, the nanorods are comprised of Au and Ag segments, the sacrificial Ag segments are removed by treating the coated nanorods with an etching solution containing methanol, 30% ammonium hydroxide, and 30% hydrogen peroxide (4:1:1 v/v/v) for one hour. Numerous other combinations of materials and etchants can likewise be used for such purposes depending upon the intended use of the structures formed.

Synthesis of Nanowires: Multi-segment nanorods composed of Ni and Au segments were synthesized using electrochemical deposition into a porous alumina membrane. A thin layer of Ag (200 μm) was evaporated on one side of an alumina filter (Whatman International Ltd, d=13 mm, pore size=20 nm; the pore diameter in the central region of the filter is substantially larger than the quoted 20 nm) and served as a cathode in a three electrode chemical cell after making physical contact with aluminum foil. Platinum wire was used as a counter electrode, and Ag/AgCl was used as the reference electrode. The nanopores were partially filled with Ag, leaving headroom to accommodate the growth of additional domains (Technic ACR silver RTU solution from Technic, Inc.) at a constant potential, −0.9 V vs. Ag/AgCl, by passing 1.5 C/cm$^2$ for 30 minutes. An Au segment then was electroplated from Orotemp 24 RTU solution (Technic, Inc.) at −0.9 V vs. Ag/AgCl followed by a Ni segment from nickel sulfamate RTU solution (Technic, Inc.) at −0.9 V vs. Ag/AgCl. The procedure involving Au was repeated to form a second Au segment. Each segment length was controlled by monitoring the charge passed through the membrane. The first 1.4 μm (+0.2) long segment of Au was generated by passing 1.3 C. The Ag backing and the alumina membrane then were dissolved with concentrated nitric acid and 3 M sodium hydroxide solutions, respectively. The rods were repeatedly rinsed with nanopure water until the solution reached at pH of 7. Nanorods containing more than three segments are prepared by repeating the above steps until the desired number of segments have been constructed. These added segments may be constructed of the same or different materials than the materials used in the construction of the initial three segments, by appropriate selection of the plating materials and conditions in the manner known to those of skill in the art.

Preparation of Segmented Nanorods Composed of Gold (Au) and Nickel (Ni) was achieved using electrochemical synthesis. The design of the structures was devised to incorporate specific distances between similar nanodisks and to separate different nanodisks beyond the diffraction of the excitation wavelength. This spatial separation allowed for discrete measurement and observation of individual classes of nanodisks.

Multi-segment nanorods and nanodisk arrays were prepared according to reported methods (Qin, L. et al, *Science* 309, 113-115 (2005)). The applied charge during electrochemical deposition was controlled to achieve designed nanorod structures. Charge and length of each sample are shown in Table 1. The resulting structures were measured by SEM (FIGS. 3A, 3B, and 4A-4F).

FIG. 3A is an SEM image of a nanorod having a diameter of 360±20 nm, composed of metal segments of, from bottom to top, 600±30 nm Au, 2 μm Ni, 300±20 nm Au, 30±5 nm Ni, 300±20 nm Au, 2 μm Ni, and then four repeating segments of 45±5 nm Au/30±5 nm Ni, and a final 45±5 nm Au segment. FIG. 3B is an SEM image of a nanowire of the nanorod of FIG. 3A after chemical etching to remove the Ni segments.

FIG. 4A is a nanorod of identical 120±10 nm Au disks with 30±5 nm Ni segments between them. From top to bottom, the number of Ni segments between each 120±10 nm Au disk is 0, 1, 2, 3, and 4. Each nanodisk array is separated by a Ni segment of 1.2 μm. FIG. 4D is an SEM image of the nanowire of the nanorod of FIG. 4A after chemical etching to remove the Ni segments.

FIG. 4B is an SEM image of a nanorod composed of varying Au disk thicknesses. From top to bottom, the Au disk thicknesses are 40±5, 80±8, 120±10, and 200±15 nm. Each disk is repeated twice, separated by a Ni segment of 30±5 nm. Each array is separated by a 1 μm Ni segment. FIG. 4E is an SEM image of the nanowire of the nanorod of FIG. 4B after chemical etching to remove the Ni segments.

FIG. 4C is an SEM image of a nanorod composed of varying Ni segments between Au segments of identical thickness, 120±10 nm. From bottom to top, the Ni segments are 160±10, 80±10, 30±5, 15±5, and 5±2 nm. The separations between nanodisk arrays is 1 μm. FIG. 4F is an SEM image of the nanowire of the nanorod of FIG. 4C after chemical etching to remove the Ni segments.

The length of the segments of nanowires obeys Faraday's law of electrolysis (See Qin, L. et al, *Science* 309, 113-115 (2005) supporting online materials). For a specific example herein, in FIG. 4C, deposition of Ni segments was controlled to adjust the distance between the gold nanodisks. Charges were applied for 1.332 C, 0.666 C, 0.251 C, 0.080 C, and 0.040 C during electrochemical deposition (Table 1). The resulting lengths of Ni segments were 160 nm, 80 nm, 30 nm, 15 nm, and 5 nm, respectively. FIG. 4C also shows that the dark stripes between the bright regions are thinner and thinner from bottom left to upper right.

Figure 3:
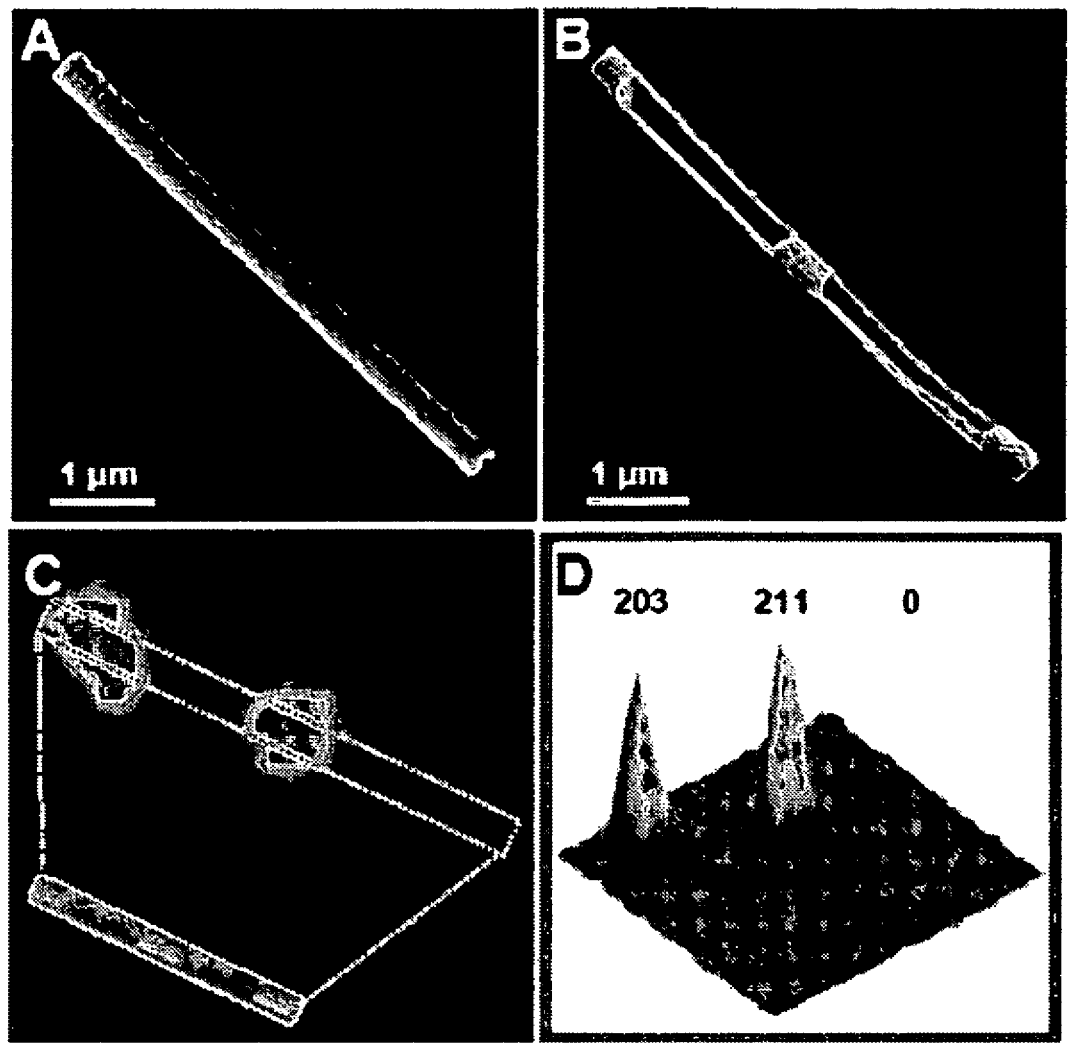
FIG. 3A is a field emission scanning electron microscopy (SEM) image of a nanowire having gold (Au) and nickel (Ni) segments prepared using OWL, wherein the nickel segments are darker than the gold segments.
FIG. 3B is an SEM image of the wire of FIG. 3A after treatment with nitric acid to remove the Ni segments, wherein the Au segments remain as arrayed nanodisks/rods.
FIG. 3C is a scanning micro Raman image (SMRI) of gapped nanowires functionalized with a Raman probe, methylene blue (MB), wherein the inset is a schematic representation of the nanowire.
FIG. 3D is a three-dimensional representation of the SMRI of FIG. 3C, wherein the peak intensities are in arbitrary units.
Figure 4:
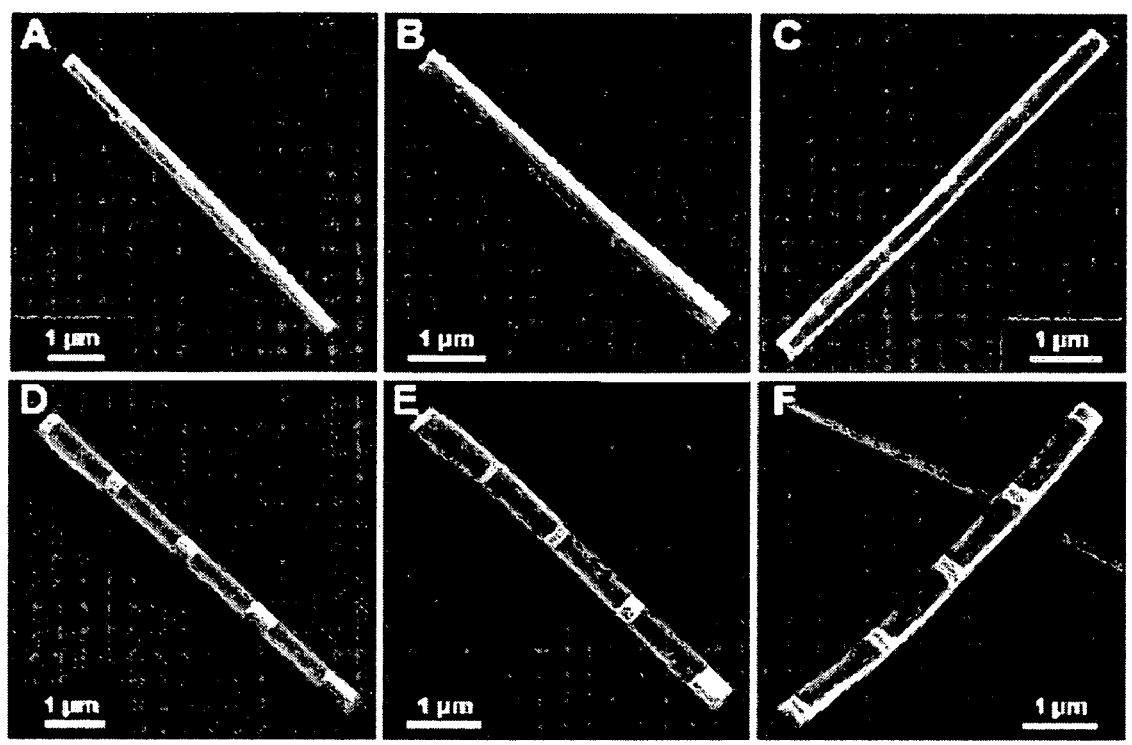
FIG. 4A is an SEM image of a nanowire prior to etching and having 120±10 nm Au disks with varying numbers of 30±5 nm Ni segments between the Au nanodisks.
FIG. 4B is an SEM image of a nanowire prior to etching having identical 30±5 nm Ni segments with varying Au disk thicknesses of 40±5, 80±8, 120±10, or 200±15 nm (from top to bottom)
FIG. 4C is an SEM image of a nanowire prior to etching having identical Au disks of 120±10 nm and Ni segments of 160±10, 80±10, 30±, 15±5, and 5±2 nm.
FIG. 4D is an SEM image of the nanowire of FIG. 4A after etching.
FIG. 4E is an SEM image of the nanowire of FIG. 4B after etching.
FIG. 4F is an SEM image of the nanowire of FIG. 4C after etching.
Figure 5:
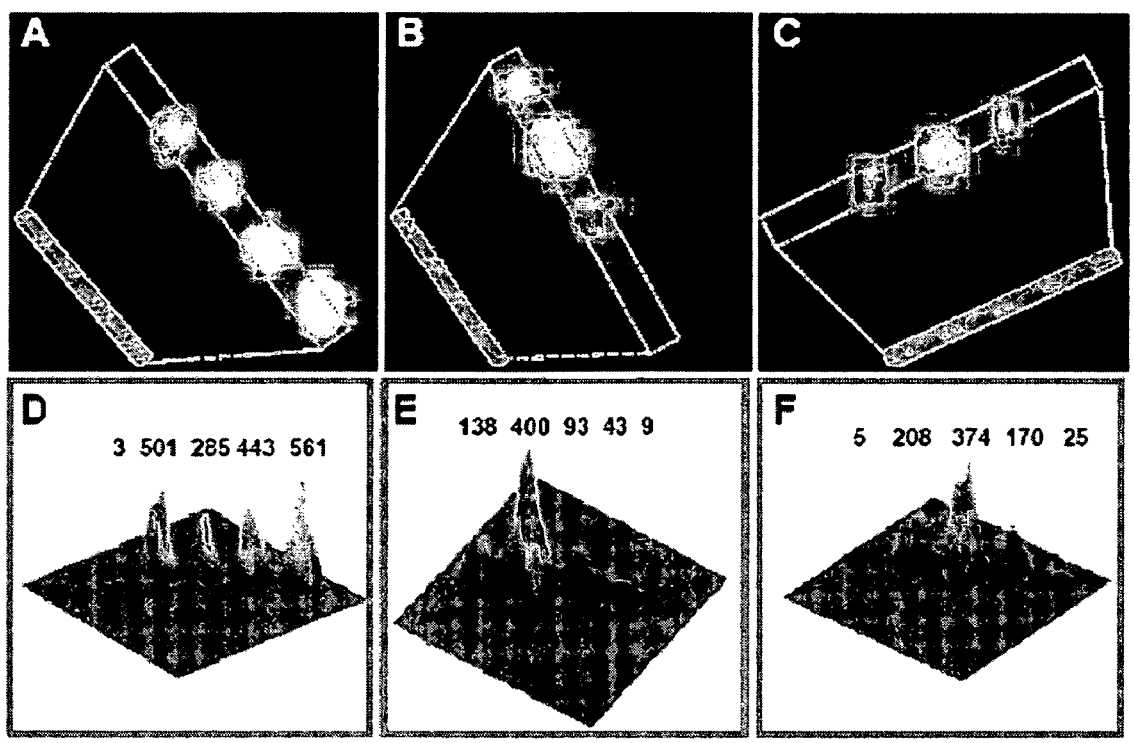
FIG. 5A is a confocal Raman microscope image of the gapped nanowire structure of FIG. 4D functionalized with a monolayer of MB.
FIG. 5B is a confocal Raman microscope image of the gapped nanowire structure of FIG. 4E functionalized with a monolayer of MB.
FIG. 5C is a confocal Raman microscope image of the gapped nanowire structure of FIG. 4F functionalized with a monolayer of MB.
FIG. 5D is a three dimensional (3 D) Raman image corresponding to the two dimensional (2 D) image of FIG. 5A, with peak intensities in arbitrary units.
FIG. 5E is a 3 D Raman image corresponding to the 2 D image of FIG. 5B, with peak intensities in arbitrary units.
FIG. 5F is a 3 D Raman image corresponding to the 2 D image of FIG. 5C, with peak intensities in arbitrary units.

Details for the production of the nanowires in FIGS. 3-5 are tabulated in the following table, wherein the amount of charge for the electrochemical deposition of the metal segments is reported in Coulombs (C) and the corresponding length of each metal segment is also reported. There are two different types of Ni segments, one for the gaps between the Au disks and one which allows for the physical separation of the various nanodisks. The role that each Ni segment plays in the final nanowire is indicated by the color coding of the table cell: Au is grey-shaded cell, no shading is Ni segments that are etched away to form gaps between Au disks, and Ni segments that are etched away to spatially separate nanodisk arrays of different properties are black-shaded.

TABLE 1

| | Figure 2A | | Figure 3A | | Figure 3B | | Figure 3C | |
|---|---|---|---|---|---|---|---|---|
| | Charge/C | Length/nm | Charge/C | Length/nm | Charge/C | Length/nm | Charge/C | Length/nm |
| | 1.400 | 600±30 | 0.300 | 120±10 | 0.100 | 40±5 | 0.300 | 120±10 |
| | 10.00 | 2000±100 | 0.251 | 30±5 | 5.00 | 1000±50 | 1.332 | 160±10 |
| | 0.700 | 300±20 | 0.300 | 120±10 | 0.100 | 40±5 | 0.300 | 120±10 |
| | 0.252 | 30±5 | 0.251 | 30±5 | 0.252 | 30±5 | 5.00 | 1000±50 |
| | 0.700 | 300±20 | 0.300 | 120±10 | 0.100 | 40±5 | 0.300 | 120±10 |
| | 10.01 | 2000±100 | 0.251 | 30±5 | 5.01 | 1000±50 | 0.666 | 80±10 |
| | 0.114 | 45±5 | 0.300 | 120±10 | 0.200 | 80±8 | 0.300 | 120±10 |
| | 0.251 | 30±5 | 0.251 | 30±5 | 0.253 | 30±5 | 5.00 | 1000±50 |
| | 0.110 | 45±5 | 0.300 | 120±10 | 0.200 | 80±8 | 0.300 | 120±10 |
| | 0.252 | 30±5 | 6.00 | 1200±60 | 5.01 | 1000±50 | 0.251 | 30±5 |
| | 0.111 | 45±5 | 0.300 | 120±10 | 0.300 | 120±10 | 0.300 | 120±10 |
| Metal Charge and Length | 0.250 | 30±5 | 0.252 | 30±5 | 0.251 | 30±5 | 5.01 | 1000±50 |
| | 0.110 | 45±5 | 0.300 | 120±10 | 0.300 | 120±10 | 0.300 | 120±10 |
| Legends: | 0.250 | 30±5 | 0.252 | 30±5 | 5.00 | 1000±50 | 0.126 | 15±5 |
| | 0.112 | 45±5 | 0.300 | 120±10 | 0.500 | 200±15 | 0.300 | 120±10 |
| | | | 0.252 | 30±5 | 0.253 | 30±5 | 5.00 | 1000±50 |
| | | | 0.300 | 120±10 | 0.501 | 200±15 | 0.300 | 120±10 |
| Au | | | 6.01 | 1200±60 | | | 0.040 | 5±2 |
| Ni for Gaps | | | 0.300 | 120±10 | | | 0.300 | 120±10 |
| Ni for Separations | | | 0.250 | 30±5 | | | | |
| | | | 0.300 | 120±10 | | | | |
| | | | 0.251 | 30±5 | | | | |
| | | | 0.300 | 120±10 | | | | |
| | | | 6.00 | 1200±60 | | | | |
| | | | 0.300 | 120±10 | | | | |
| | | | 0.250 | 30±5 | | | | |
| | | | 0.300 | 120±10 | | | | |
| | | | 6.00 | 1200±60 | | | | |
| | | | 0.300 | 120±10 | | | | |

Surface Enhanced Raman Scattering

Gapped nanowires having gold nanodisks and a silicon dioxide coating were prepared using OWL, then were mixed with 1 µM methylene blue (MB), a Raman active molecule, in ethanol and stirred overnight. The solution was centrifuged and redispersed in ethanol five times to remove any non-dissociated MB. The resulting gold nanowires coated with a self-assembled monolayer of MB were concentrated by centrifugation and dried onto a pirhana-pretreated glass substrate.

Using a scanning Raman microscope, Raman scattering of the substrates was obtained by monitoring the strong Raman band at 1621 cm$^{-1}$ and reconstructing the image pixel by pixel. The incident laser wavelength was 633 nm. In situ optical images were also taken, which provided position and orientation information for the gapped nanowires.

The Raman microscopy results (see FIG. 3C and FIG. 3D) shows that scattering from disks separated by nanosize gaps is dramatically more intense than from disks without a gap. The difference in Raman intensities between two disks with one gap and five disks with four gaps was not significant, although the spot area for structures with four gaps is larger than those with one gap, due to the larger overall surface area for the latter (see FIG. 5A and FIG. 5D).

A systematic study of gap number, disk thickness, and gap size dependence of SERS intensities was carried out. FIGS. 4A, 4B, and 4C present SEM images of Au—Ni mulicomponent nanowires. After performing OWL, the corresponding gapped nanowires were obtained as shown in FIGS. 4D, 4E, and 4F. The SEM images provided more precise sizes in FIG. 4A, FIG. 4B, and FIG. 4C than in FIG. 4D, FIG. 4E, and FIG. 4F due to the charges accumulated on the coated SiO$_2$ layer during electron beam scanning.

A Raman scattering investigation was carried out with the structures of FIG. 4. The resulting images are shown in FIG. 5. FIGS. 5A, 5B, and 5C are 2 D Raman scattering images and FIGS. 5D, 5E, and 5F are the corresponding 3 D images. The insets in FIGS. 5A, 5B, and 5C show the structural information for the corresponding Au disks.

Raman spectra and images were recorded with a confocal Raman microscope (CRM200 WiTec) equipped with a piezo scanner and 100× microscope objectives (NA=0.90, Nikon). Spatial resolution is as high as 400 nm in this experiment.

Samples were excited with a He—Ne laser (632.8 nm, Coherent Inc.) with a spot size of about 1 µm and a power density of about 10$^4$ W/cm$^2$ incident on the samples. For a typical Raman image with a scan range of 10 µm×10 µm, complete Raman spectra were acquired on every pixel with an integration time of 0.1 second (s) per spectrum and an image resolution of 100 pixel×100 pixel. To provide a careful analysis of the enhanced Raman scattering signal of MB on the sample features, all images in the figures were processed by integrating the intensity of the Raman spectra at 1621 cm$^{-1}$. The SERS spectra of both MB and pMA with different concentrations were obtained with 1 second integration time. MB shows a strong absorption band at about 655 nm, which increases the SERS signal intensity under excitation at 632.8 nm.

The laser excitation wavelength was at 633 mm, which is close to the absorption energy of the MB molecule. As shown in FIG. 5A, four bright spots were easily observable, which correspond to the Raman scattering signals from the nanodisk arrays having one, two, three, and four gaps. The spot sizes became larger when gap number increased due to the larger gap areas and therefore increased number of dye molecules in locations with larger SERS enhancements. The signal for two disks with one gap was 167 times higher than that from one disk without a gap. This provided significant insight into the electromagnetic mechanism of SERS and facilitated the design of SERS substrates, indicating that a gap is important to the ability of a metal surface to enhance Raman scattering.

The influence of particle size and gap distance on SERS intensities also was investigated. The disk thickness dependence of the intensities is shown in FIG. 5B. The disk gap was fixed at 30 mm with disk thicknesses varying from 40 to 160 nm. A single disk with a 40 nm thickness was also included at one end of the structure as a control. A 2 D image showed five spots of Raman scattering signals from the Au disks with different size and an identical gap distance (FIG. 5B). The spot from the 120±20 nm Au disks showed the maximum enhanced Raman scattering signal. The 3 D image in FIG. 5E revealed the differences more clearly.

In FIG. 5C, the disk thickness was fixed at 120 mm, and the gap distances varied from 5 to 160 mm: The intensities of the spots in the 2 D images increased initially, peaked at the 30 nm gap distance, then declined with increasing gap distance. The corresponding 3 D image (FIG. 5F) shows how the peak intensity changes with disk spacing.

A theoretical treatment of the Au nanodisks was also performed. The local electric fields |E|$^2$ between two cylindrical gold nanodisks in vacuum was calculated using the discrete dipole approximation (DDA) method. (Kelly et al., *J. Phys. Chem. B* 107: 668 (2003)) The SiO$_2$ film was not included in the calculations. The working wavelength in calculating the enhanced local electric fields between the Au nanodisks was chosen to be the excitation wavelength of 633 nm, in order to mimic the experiments performed with MB. The results with 669 nm (the mean of the incident and Stokes-shifted wavelengths) also was investigated, and the results were similar. The grid size used in the DDA program was 5 nm. The polarizations both parallel and perpendicular to the interdimer axis were studied, and are indicated as the Z and Y axes, respectively. For a disk diameter of 360 nm, the resonance wavelengths for these two polarizations are similar. However, the SERS enhancements are only large for Z polarization, and the variation of the Z-polarized resonance behavior with interdisk spacing is important to the interpretation of the experiments.

Figure 6:
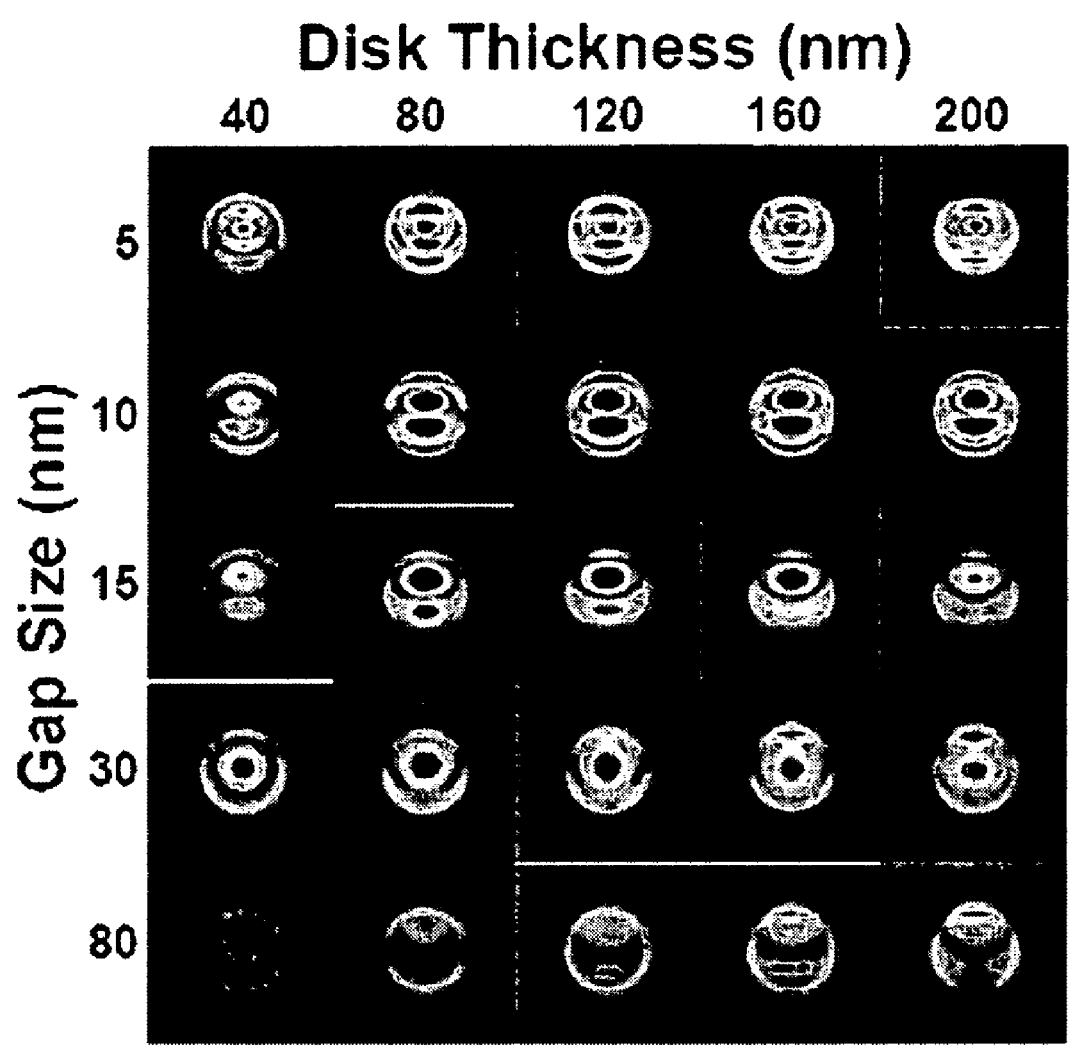
FIG. 6 contains the electric field enhancement for disk dimmers composed of identical Au disks having different thicknesses and gap distances.

Contours of the electric fields (plotted as |E|$^2$) for a two nanodisk array with different disk thicknesses and gaps are shown in FIG. 6. The plane used for the intensity calculation is between the two disks and 5 nm above the surface of one of them (the choice does not effect the calculations). Each column represents nanodisk arrays with the same thickness while each row represents nanodisk arrays with the same gap distance. The disk thicknesses from left to right are 40, 80, 120, 160, and 200 nm, respectively. The gap distances from top to bottom are 5, 10, 15, 30, and 80 nm, respectively. The contours range from 0-50 times the incident intensity. The 120 nm thick disks show the largest peak electric fields (|E|$^4$ maximizes at 105 times the incident field intensity) and also the highest average fields (<|E|$^4$>=1700, where the average is over the entire surface area of both particles). This dependence of the results on disk thickness is in agreement with the experimental measurements (see FIG. 5E). The magnitude of the SERS enhancement factor compared to that for an isolated disk (where <|E|$^4$>=18) was accurately predicted. Previous studies (Hao et al., *J. Chem. Phys.* 120: 357 (2004)) focused on the electric fields around silver particle triangles and found that the electric fields between the particles increase dramatically with decreasing gap size. However, in this simulation, the electric fields (both peak and average) are found to peak at a 10 nm gap distance. For example, $<|E|^2>$ is 1700 for 120 nm thick disks with a 10 nm gap, while the number declines to 300 when the gap distance narrows to 5 nm, and to 190 when the gap distance increases to 15 nm. These calculations are in qualitative agreement with the experimental observations, except that the gap distance with the highest Raman signals occur at 30 nm. Although the gaps between particles generally lead to enhanced fields, the decline in enhancement for very small gaps arises due to the detuning of the dipole plasmon mode to the red of the excitation and Stokes shifted wavelengths. This is apparent from FIG. 6, which shows an increased number of nodes in the field as the gap is decreased due to excitation of higher multipoles. Although higher multipoles still produce strong scattering at 633 nm, the field enhancements associated with these modes are smaller than for a dipole mode. This situation is more complicated in the experiment due to the surface roughness in the gap, but the theory and experiments are in quantitative agreement.

The foregoing describes and exemplifies the invention but is not intended to limit the invention defined by the claims which follow. All of the methods disclosed and claimed herein can be made and executed without undue experimentation in light of the present disclosure. While the materials and methods of this invention have been described in terms of specific embodiments, it will be apparent to those of skill in the art that variations may be applied to the materials and/or methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those of ordinary skill in the art are deemed to be within the spirit, scope and concept of the invention as defined by the appended claims.

What is claimed is:

1. A method of assaying for a presence or a concentration of an analyte or a plurality of analytes in a sample comprising:
   a) contacting the sample with a nanowire to create a mixture, wherein the nanowire comprises at least one nanodisk array comprising at least two nanodisks, each nanodisk independently having a thickness of about 20 nm to about 500 nm, and at least one gap of about 2 to about 500 nm;
   b) illuminating the mixture with a radiation source; and
   c) measuring a signal intensity resulting from the illumination of the mixture, wherein the intensity is correlated to the presence or concentration of the analyte in the sample.

2. The method of claim 1 wherein the nanodisk array comprises nanodisks having a thickness of about 40 to about 250 nm.

3. The method of claim 1 wherein the nanodisk array comprises gaps of about 5 to about 160 nm.

4. The method of claim 1 wherein the nanodisks are gold.

5. The method of claim 1 wherein the number of gaps in the nanodisk array is selected from the group consisting of 1, 2, 3, 4, 5, 6, 7, 8, 9, and 10.

6. The method of claim 1 wherein the sample further comprises a detection reagent.

7. The method of claim 6 wherein the detection reagent is capable of covalently attaching to the analyte.

8. The method of claim 6 wherein the detection reagent is capable of non-covalently attaching to the analyte.

9. The method of claim 1 wherein the radiation source is a laser.

10. The method of claim 1 wherein the signal intensity is enhanced compared to a signal intensity when the sample is assayed in the absence of the nanowire.

11. The method of claim 10 wherein the signal intensity is enhanced by factor of about 10 to about 200 times more intense than a signal intensity when the sample is assayed in the absence of the nanowire.

12. The method of claim 10 wherein the signal intensity is amplified due to a plasmon resonance.

13. The method of claim 1 wherein the signal is a surface enhanced Raman scattering signal.

14. A kit for practicing the method of claim 1 comprising a plurality of nanowires, wherein each nanowire comprises at least one nanodisk array comprising at least two nanodisks, at least one gap, and a coating to hold the nanodisk arrays in the nanowire, wherein each nanodisk independently has a thickness of about 20 nm to about 500 nm, and each gap independently is about 2 to about 500 nm, and
   wherein the nanodisk arrays are capable of a signal intensification due to a plasmon resonance.

15. The kit of claim 14 further comprising one or more of detection reagents or probes.

* * * * *